United States Patent
Fabbri et al.

(10) Patent No.: US 10,668,110 B2
(45) Date of Patent: Jun. 2, 2020

(54) THERAPEUTIC COMBINATION COMPRISING A PULMONARY SURFACTANT AND A STEROID FOR THE TREATMENT OF EVOLVING BPD

(71) Applicant: CHIESI FARMACEUTICI S.p.A., Parma (IT)

(72) Inventors: Laura Fabbri, Parma (IT); Fabrizio Salomone, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 90 days.

(21) Appl. No.: 15/850,546

(22) Filed: Dec. 21, 2017

(65) Prior Publication Data

US 2018/0177832 A1 Jun. 28, 2018

(30) Foreign Application Priority Data

Dec. 22, 2016 (EP) .................... 16206232

(51) Int. Cl.
*A61K 45/06* (2006.01)
*A61K 35/42* (2015.01)
*A61P 11/00* (2006.01)
*A61K 9/00* (2006.01)
*A61K 31/58* (2006.01)

(52) U.S. Cl.
CPC ............. *A61K 35/42* (2013.01); *A61K 9/007* (2013.01); *A61K 31/58* (2013.01); *A61K 45/06* (2013.01); *A61P 11/00* (2018.01); *A61K 2300/00* (2013.01)

(58) Field of Classification Search
None
See application file for complete search history.

(56) References Cited

U.S. PATENT DOCUMENTS

| | | | |
|---|---|---|---|
| 2006/0040860 A1* | 2/2006 | Ruediger | A61K 38/1866 424/450 |
| 2006/0194728 A1* | 8/2006 | Killian | A61K 31/00 514/120 |
| 2007/0225233 A1* | 9/2007 | Yeh | A61K 9/0082 514/23 |
| 2014/0142021 A1* | 5/2014 | Johansson | C07K 14/785 514/1.5 |
| 2017/0212133 A1* | 7/2017 | Greene | C12Q 1/6883 |
| 2018/0110948 A1* | 4/2018 | Dellaca | A61M 16/0051 |

FOREIGN PATENT DOCUMENTS

| WO | 2006/074296 | 7/2006 |
|---|---|---|
| WO | 2010/136153 | 12/2010 |

OTHER PUBLICATIONS

Yeh, T. et al. Intratracheal Administration of Budesonide/Surfactant to Prevent Bronchopulmonary Dysplasia. American J of Respiratory and Critical Care Medicine 193(1)86-95, Jan. 1, 2016. (Year: 2016).*
European Search Report in Application No. 16206232.7 dated Jun. 22, 2017.
International Search Report in Application No. PCT/EP2017/083643 dated May 7, 2018.
Baveja et al., "Pharmacological Strategies in the Prevention and Management of Bronchopulmonary Dysplasia", Seminars in Perinatology, vol. 30, No. 4 (2006) pp. 209-218.
Schulzke S M et al., "The management of evolving bronchopulmonary dysplasia", Paediatric Respiratory Reviews, vol. 11, No. 3 (2010) pp. 143-148.
Kuo H T et al., "A Follow-Up Study of Preterm Infants Given Budesonide Using Surfactant as a Vehicle to Prevent Chronic Lung Disease in Preterm Infants", The Journal of Pediatrics, vol. 156, No. 4 (2010) pp. 537-541.
M. Laughon et al., "A Pilot Randomized, Controlled Trial of Later Treatment With a Peptide-Containing, Synthetic Surfactant for the Prevention of Bronchopulmonary Dysplasia", Pediatrics, vol. 123, pp. 89-96 (2009).

* cited by examiner

*Primary Examiner* — Ralph J Gitomer
(74) *Attorney, Agent, or Firm* — Oblon, McClelland, Maier & Neustadt, L.L.P.

(57) ABSTRACT

Administering a pulmonary surfactant and a corticosteroid is effective for the treatment of evolving bronchopulmonary dysplasia (BPD) in preterm neonates.

14 Claims, 7 Drawing Sheets

THERAPEUTIC COMBINATION COMPRISING A PULMONARY SURFACTANT AND A STEROID FOR THE TREATMENT OF EVOLVING BPD

CROSS REFERENCES TO RELATED APPLICATIONS

This application claims priority to European Patent Application No. 16206232.7, filed on Dec. 22, 2016, which is incorporated herein by reference in its entirety.

BACKGROUND OF THE INVENTION

Field of the Invention

The present invention relates to compositions for the treatment of diseases of prematurity. The present invention also relates to methods for the treatment of diseases of prematurity.

Discussion of the Background

The human lung is composed of a large number of small air sacs, called alveoli, in which gases are exchanged between the blood and the air spaces of the lungs. In healthy individuals, this exchange is mediated by the presence of a protein-containing surfactant complex that prevents the lungs from collapsing at the end of expiration.

The lung surfactant complex is composed primarily of lipid and contains minor amounts of various proteins. An absence of adequate levels of this complex results in malfunction of the lungs. This syndrome is called Respiratory Distress Syndrome (RDS) and it commonly affects preterm neonates.

The mainstay of the treatment of RDS is the replacement therapy with exogenous pulmonary surfactant preparations extracted from animal lungs, known as modified natural surfactants. For instance, modified natural surfactants used in the clinical practice are poractant alfa derived from porcine lung, and sold under the trademark of Curosurf®, beractant (Surfacten® or Survanta®) bovactant (Alveofact®), both derived from bovine lung, and calfactant derived from calf lung)(Infasurf®).

Exogenous pulmonary surfactants are currently administered by endotracheal instillation as a suspension in a saline aqueous solution to intubated pre-term infants kept under mechanical ventilation with oxygen.

Although said therapy has greatly increased postnatal survival, children that survive RDS have a high risk of developing broncho-pulmonary dysplasia (BPD), a common and serious complication of prematurity, associated with significant mortality, morbidity and healthcare resource utilization. Despite advances in both prenatal and neonatal care the incidence of the condition continues to rise. The management of BPD and its related problems remains a major challenge for neonatologists and paediatricians. Multiple interventions have been proposed to prevent and treat BPD but many are still not evidence based. Current treatments appear to have reduced the severity of BPD but have had little effect on its incidence. BPD is an evolving process of lung injury and its pathophysiology varies at different stages of the disease. Its management therefore is unlikely to be in the form of a single intervention but rather a combined approach with different strategies used to target different factors and/or stages of the disease.

For this reason, it is useful to categorize intervention for BPD at three subsequent stages when designing an overall management plan. These are: i) prevention of BDP; ii) treatment of evolving BPD; and iii) treatment of established BPD (see Bowen P et al Pediatrics and Child Health 2013, 24:1, 27-31, which is incorporated herein by reference in its entirety).

The prevention of BPD in neonates affected by RDS has been managed by systemic administration of a corticosteroid, antenatal or within few hours postnatal. However, the effectiveness of postnatal corticosteroid administration is offset by possible adverse systemic effects, e.g., hypertension, hyperglycemia, gastrointestinal complications, and neurodevelopmental disability.

As an alternative to systemic administration, delivery of corticosteroid by inhalation or intracheal instillation has been proposed for the prophylaxis of BDP.

For example, US 2010/0317636, which is incorporated herein by reference in its entirety, discloses a method for the prophylaxis of BPD in an infant suffering from respiratory distress syndrome by administering to the infant a combination of a corticosteroid having a high local to systemic anti-inflammatory activity and a lung surfactant.

Yeh et al (Pediatrics 2008, 121(5), e1310-e1318, which is incorporated herein by reference in its entirety) proposed the intratracheal instillation of budesonide using the pulmonary surfactant Survanta® as a carrier, while Dani et al (Pediatr Pulmonol 2009, 44, 1159-1167, which is incorporated herein by reference in its entirety) have proposed the intratracheal instillation of beclometasone dipropionate in combination with Cursourf®.

However, through these approaches as well, a large population of preterm neonates would be exposed to corticosteroids, many without benefit if otherwise they would not develop BPD (see Bancalari E Am J Respir Crit Care Med 2016, 193:1, 12, which is incorporated herein by reference in its entirety).

On the other hand, serious concerns were raised on the efficacy of corticosteroids in established BDP, as said disease is hallmarked by strong and persistent airway inflammation, fibrosis, and smooth muscle hypertrophy.

Postnatal corticosteroids could find their place in therapy in the treatment of evolving BPD as in this way they will be administered to patients in need thereof.

However, due to the observed side effects or to the lack of clear sign of efficacy, the systemic postnatal administration of dexamethasone and hydrocortisone is not currently recommended routinely.

In view of the above considerations, there is still a need to develop a more compliant corticosteroid-based medicament for the treatment of evolving BPD in premature neonates.

Furthermore, it would be advantageous to provide a medicament that may be administered locally either by inhalation or intra-tracheal instillation.

Finally, it would be of particular advantage to provide a medicament able of promoting the lung development.

SUMMARY OF THE INVENTION

Accordingly, it is one object of the present invention to provide novel compositions for the treatment of diseases of prematurity.

It is another object of the present invention to provide novel methods for the treatment of diseases of prematurity.

These and other objects, which will become apparent during the following detailed description, have been achieved by the inventors' discovery that administration of a pulmonary surfactant in combination with budesonide is useful for the treatment of evolving bronchopulmonary dysplasia (BPD) in preterm neonates.

Thus, the present invention provides the use of a pulmonary surfactant in combination with a steroid for treating evolving broncho-pulmonary dysplasia in preterm neonates.

Accordingly, in one embodiment, the present invention is directed to a pulmonary surfactant in combination with budesonide at a dose of 0.1 to 1.5 mg/kg for use for the treatment of evolving bronchopulmonary dysplasia (BPD) in preterm neonates.

Preferably, the combination of the invention increases the mRNA expression of some protein indicators of lung maturation, more preferably the mRNA expression of the surfactant proteins SP-A, SP-B and SP-C.

Advantageously, said combination is administered from the $2^{nd}$ to the $28^{th}$ day of life, preferably from the $5^{th}$ to the $15^{th}$ day of life, more preferably from the $7^{th}$ to the $10^{th}$ day of life.

The present invention is also directed to the use of a pulmonary surfactant in combination with budesonide at a dose of 0.1 to 1.5 mg/kg in the manufacture of a medicament for the treatment of bronchopulmonary dysplasia (BPD) in preterm neonates.

Advantageously, said combination is administered from the $2^{nd}$ to the $28^{th}$ day of life, preferably from the $5^{th}$ to the $15^{th}$ day of life, more preferably from the $7^{th}$ to the $10^{th}$ day of life.

Preferably the dose of budesonide is 0.2 to 1.0 mg/kg.

The medicament of the present invention could be administered simultaneously, sequentially or separately, preferably for simultaneous administration as fixed combination.

In a particular embodiment, said medicament is in the form of pharmaceutical composition for inhalation or intratracheal administration comprising said fixed combination.

In a further embodiment, the present invention is directed to a method for the treatment of evolving bronchopulmonary dysplasia comprising the administration to a preterm infant in need of such treatment a pulmonary surfactant in combination with budesonide at a dose of 0.1 to 1.5 mg/kg, wherein said combination is administered from the $2^{nd}$ to the $28^{th}$ day of life, preferably from the $5^{th}$ to the $15^{th}$ day of life, more preferably from the $7^{th}$ to the $10^{th}$ day of life.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
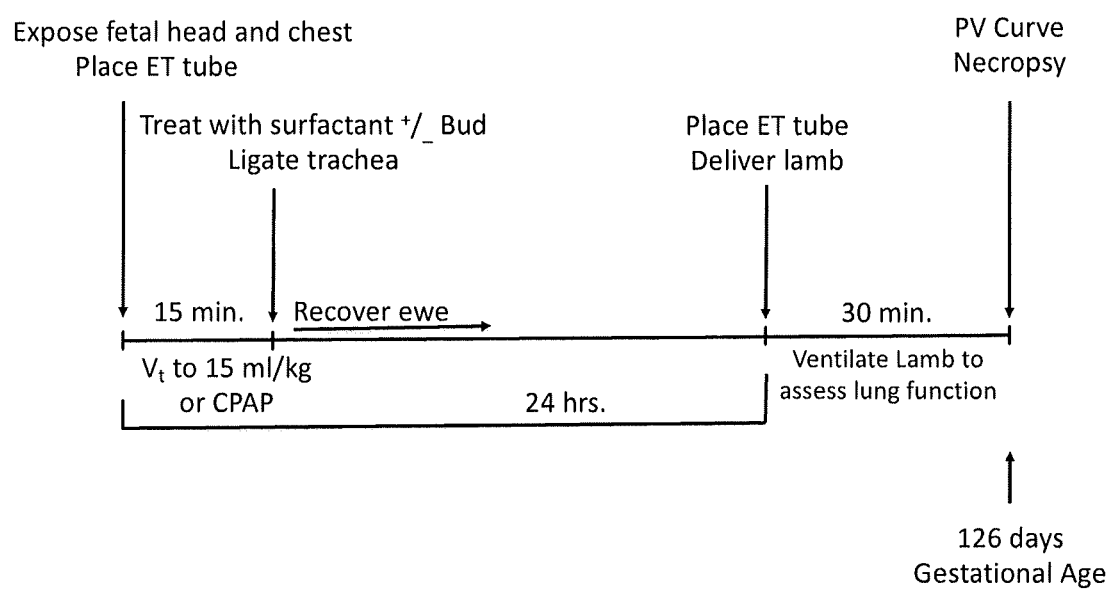
FIG. 1 i a scheme of the protocol for this complex series of interventions.

The term "bronchopulmonary dysplasia (BPD)" refers to a chronic pulmonary disorder, also known as chronic lung disease (CLD), which is the consequence of unresolved or abnormally repaired lung damage.

BPD typically occurs in very low birth weight (VLBW) infants who sustain lung damage as a result of oxygen toxicity and barotrauma from mechanical ventilation early in life. The definition and classification of BPD have changed since its original description by Northway et al. in 1967. The National Institute of Child Health and Human Development (NICHD) defined BPD in a consensus statement in 2001. This definition uses supplemental oxygen requirement for 28 days and then identifies 3 grades of severity, dependent on the respiratory support required at either 36 weeks postmenstrual age (PMA) or at discharge for those born at <32 weeks gestation or at 56 days of life or discharge for those born at >32 weeks gestation.

According to more recent definitions, BPD may be primarily considered an arrest of lung development (see Jobe A et al Ped Res 1999, 46, 641, which is incorporated herein by reference in its entirety).

In 2001 Jobe A et al (*Am J Respir Crit Care Med;* 163(7) 1723-1729, which is incorporated herein by reference in its entirety) proposed a new definition including specific criteria for 'mild,' 'moderate' and 'severe' BPD.

Mild BDP is defined as the disease requiring supplemental oxygen for ≥28 days and on room air at 36 weeks PMA or at discharge (for infants <32 weeks at birth) or at 56 days or at discharge (for infants ≥32 weeks at birth).

Moderate BDP is defined as the disease requiring supplemental oxygen for ≥28 days and a need for supplemental oxygen <30% at 36 weeks PMA/discharge (for <32 weeks) or at 56 days/discharge (for infants ≥32 weeks).

Severe BPD is defined as the disease requiring supplemental oxygen for ≥28 days and a need for ≥30% oxygen or on nasal CPAP or mechanical ventilation at 36 weeks PMA/discharge (<32 weeks) or at 56 days/discharge (≥32 weeks).

The term "evolving BPD", sometimes known as early BPD, refers to the initial phase of the chronic process leading to established BDP and indicates the disease characterized by oxygen and/or ventilator-dependency from $7^{th}$ to $14^{th}$ day of life (Walsh M C et al Pediatrics 2006, 117, S52-S56, which is incorporated herein by reference in its entirety).

The term "modified natural surfactant" refers to a lipid extract of minced mammalian lung. Due to the lipid extraction process used in the manufacture process, the hydrophilic proteins SP-A and SP-D are lost. These preparations have variable amounts of two hydrophobic, surfactant-associated proteins SP-B and SP-C and, depending on the method of extraction, may contain non-surfactant lipids, proteins or other components.

The term "poractant alfa" refers to a modified natural surfactant extracted from porcine lungs substantially consisting of polar lipids, mainly phospholipids and the proteins, SP-B and SP-C. Poractant alfa is available under the trademark Curosurf®.

The term "artificial" pulmonary surfactants refers to simply mixtures of synthetic compounds, primarily phospholipids and other lipids that are formulated to mimic the lipid composition and behavior of natural pulmonary surfactant. They are devoid of pulmonary surfactant proteins.

The term "reconstituted" pulmonary surfactants refers to artificial pulmonary surfactants to which have been added pulmonary surfactant proteins/peptides isolated from animals or proteins/peptides manufactured through recombinant technology such as those described in WO 95/32992, which is incorporated herein by reference in its entirety, or synthetic pulmonary surfactant protein analogues such as those described in WO 89/06657, WO 92/22315, and WO 00/47623, all of which are incorporated herein by reference in their entireties.

The term "non-invasive ventilation (NIV) procedure" defines a ventilation modality that supports breathing without the need for intubation such as nasal Continuous Positive Airway Pressure (nasal CPAP). Other non-invasive ventilation procedures are nasal intermittent positive-pressure ventilation (NIPPY), High Flow Nasal Cannula (HFNC), and bi-level positive airway pressure (BiPAP).

The term "respiratory support" includes any intervention that treats respiratory illness including, for example, the administration of supplemental oxygen, mechanical ventilation, and nasal CPAP.

The term "treatment" refers to the use for curing, symptom-alleviating, symptom-reducing of the disease or condition, e.g., BPD in the patient.

The term "prevention" refers to the use for progression-slowing and/or onset delaying of the disease or condition, e.g., BPD, in the patient.

The term "pre-term neonates", or preterm infants, includes extremely low birth weight (ELBW), very-low-birth-weight (VLBW), and low-birth weight (LBW) neonates of 24 to 35 weeks gestational age.

The term "fixed combination" means a combination wherein the active substances are in a fixed quantitative ratio.

"Pharmaceutical acceptable" is a term used herein that refers to a medium that does not produce an allergic or similar untoward reaction when administered to an infant.

"Surfactant activity" for a surfactant preparation is defined as the ability to lower the surface tension.

The in vitro efficacy of exogenous surfactant preparations is commonly tested by measuring their capability of lowering the surface tension using suitable apparatus such as Wilhelmy Balance, Pulsating Bubble Surfactometer, Captive Bubble Surfactometer and Capillary Surfactometer.

The in vivo efficacy of exogenous surfactant preparations is tested by measuring lung mechanics in pre-term animal models according to known methods.

In the context of the present description, the term "synergistic" means that the activity of the pulmonary surfactant plus that of budesonide is more than would be expected by that of the surfactant or the budesonide alone.

With the term "biosimilar of poractant alfa," it is meant a modified natural pulmonary surfactant which has the same safety profile, it is therapeutically equivalent, it has a similarity in the quali-quantitative composition of at least 80% (in particular regarding phospholipid and surfactant proteins SP-B and SP-C) and it has a viscosity equal to or less than 15 mPas (cP) at room temperature when it is suspended in an aqueous solution at a concentration of 80/mg/ml. The viscosity can be determined according to methods known in the art.

The present invention is based in part on the unexpected finding that budesonide at a dose of 0.1 mg/kg to 1.5 mg/kg could be combined with a pulmonary surfactant such as poractant alfa to treat evolving bronchopulmonary dysplasia (BPD) without altering the surface activity of the surfactant.

The advantages of combining a pulmonary surfactant with the claimed dose of budesonide will be apparent from the following findings.

It has indeed surprisingly been found, in a study in preterm lambs with RDS subjected to nasal CPAP ventilation, that a pulmonary surfactant such as poractant alfa in combination with budesonide significantly increases the mRNA expression of some protein indicators of lung maturation, while unexpectedly the pulmonary surfactant alone caused a decrease in such an mRNA expression.

The addition of budesonide also increases significantly the lung gas volume as well as decreases the lung weight relative to pulmonary surfactant alone.

The decrease of lung weight is in turn linked to a loss of water that indicate loss of mesenchymal cells and a maturation response.

Furthermore, the addition of budesonide to the surfactant decreases the airways wall thickness as well the collagen deposition, both indexes of lack of lung maturation.

Since budesonide is a highly lipophilic corticosteroid, this might favor its mucosal absorption and uptake across phospholipid cell membranes with a negligible systemic absorption, making the combination safe for therapeutic use in preterm neonates.

On the other hand, the pulmonary surfactant may favor the spreading of the corticosteroid by the Marangoni effect, favoring its distribution and hence the reaching of all the interested pulmonary area.

Any pulmonary surfactant currently in use, or hereafter developed for use in respiratory distress system and other pulmonary conditions could be suitable for use in the present invention. These include modified natural, artificial and reconstituted pulmonary surfactants.

Current modified natural pulmonary surfactants include, but are not limited to, bovine lipid pulmonary surfactant (BLES™, BLES Biochemicals, Inc. London, Ont), calfactant (Infasurf™, Forest Pharmaceuticals, St. Louis, Mo.), bovactant (Alveofact™, Thomae, Germany), bovine pulmonary surfactant (Pulmonary surfactant TA™, Tokyo Tanabe, Japan), poractant alfa (Curosurf™, Chiesi Farmaceutici SpA, Parma, Italy), and beractant (Survanta™, Abbott Laboratories, Inc., Abbott Park, 111).

Examples of reconstituted surfactants include, but are not limited to, the compositions disclosed in EP 2 152 288, WO 2008/011559, WO 2013/120058, all of which are incorporated herein by reference in their entireties, the products lucinactant (Surfaxin™, Windtree-Discovery Laboratories Inc., Warrington, Pa.) and the product having the composition disclosed in Table 2 of Example 2 of WO 2010/139442, which is incorporated herein by reference in its entirey, i.e.

1.5% of SP-C33(leu) acetate;
0.2% of Mini-B(leu) acetate; and
DPPC:POPG in a 50:50 weight ratio.

The pulmonary surfactant selected for use in the medicament of the present invention can be the same as, or different from, the pulmonary surfactant utilized for RDS. In a preferred embodiment, the same pulmonary surfactant is used.

In a preferred embodiment, the pulmonary surfactant is a modified natural pulmonary surfactant.

More preferably the pulmonary surfactant is poractant alfa (Curosurf™) as it is endowed with very low viscosity, and hence it can be administered at high concentrations using a small volume of aqueous carrier.

In another embodiment, the pulmonary surfactant is a reconstituted surfactant having the composition disclosed in Table 2 of Example 2 of WO 2010/139442, which is incorporated herein by reference in its entirety.

The dose of the pulmonary surfactant to be administered will vary with the weight and gestational age of the preterm neonate, as well as with the severity of the neonate condition. Those of skill in the relevant art will be readily able to determine these factors and to adjust the dosage accordingly.

Advantageously, the dose of the pulmonary surfactant could be of 100 to 200 mg/kg.

In a preferred embodiment of the present invention, poractant alfa at a dose of 100 to 200 mg/kg could be used.

In a preferred embodiment, the dose could be of 100 mg/kg, while in another preferred embodiment, the dose could be of 200 mg/kg.

Advantageously, the dose of budesonide is 0.1 to 1.5 mg/kg, more advantageously 0.2 to 1.0 mg/kg, even more advantageously 0.25 to 1.0 mg/kg.

In certain embodiments, when an effect on the lung maturation is primarily pursued, the dose of budesonide might be 0.1 to 0.5 mg/kg, while in other embodiments the dose of budesonide might be 0.5 to 1.0 mg/kg.

Preferably, the combination of the invention is administered to pre-term neonates kept under non-invasive ventilation procedures, more preferably kept under nasal CPAP, even more preferably with a nasal device, at a pressure of from 1 to 12 cm water.

The active substances of the combination of pulmonary surfactant and budesonide at the claimed doses may be administered sequentially, separately or together. Advantageously, when the two active substances are administered together, they are administered as a fixed combination.

Therefore, the present invention also provides the use of the combination of the invention as a fixed combination in the manufacture of a medicament for treating evolving BPD.

The medicament may be in form of pharmaceutical composition.

Said formulations may be administered in the form of a solution, dispersion, suspension or dry powder. Preferably, said compositions comprise the claimed combination suspended in a suitable physiologically tolerable solvent.

More preferably, the formulation comprises an aqueous solution, preferably sterile, which may also comprise pH buffering agents and other pharmaceutically acceptable excipients such as polysorbate 20, polysorbate 80 or sorbitan monolaurate as wetting agents and sodium chloride as isotonicity agent.

The formulations may be distributed in unit-dose or multi-dose containers, for example sealed ampoules and vials, or may be stored in a frozen or freeze-dried (lyophilized) condition requiring only the addition of sterile liquid carrier immediately prior to use.

Preferably, the formulation is supplied as sterile suspension in a buffered physiological saline (0.9% w/v sodium chloride) aqueous solution in single-use vials.

The administration of the claimed formulation may be carried out according to known methods, e.g. by endotracheal instillation, by spray administration, or nebulization by jet ultrasonic, or mesh-vibrating nebulisers commonly available on the market.

When the formulation is administered by endotracheal instillation, depending on the severity of the respiratory distress syndrome, different methods can be appropriate. For example the claimed formulation may be administered through the endotracheal tube to pre-terns neonates kept under mechanical ventilation.

Alternatively, the formulation may be administered by the use of a thin catheter placed in the trachea and the neonate respiration supported through specially designed nasal devices such as masks, prongs or tubes according to methodology known as nasal Continuous Positive Airway Pressure (nCPAP), according to the procedure described in. WO 2008/148469, which is incorporated herein by reference in its entirety.

The latter approach would be only possible with an exogenous surfactant such as poractant alfa having a low viscosity, as a high viscosity would make the passage of the surfactant through the thin catheter more difficult.

The volume of the aqueous solution in which the two combined active substances are suspended will depend on the desired concentration.

Advantageously, the volume of the formulation should be not more than 5.0 ml, preferably from 4.5 to 2.0 ml, more preferably 3.5 to 2.5 ml.

In other embodiments, when the pulmonary surfactant and budesonide are administered separately, the individual active substances could be formulated separately. In this case, the two individual active substances do not unconditionally have to be taken at the same time.

In the case of such a separate administration, the formulation of the two individual active substances can be packed at the same time in a suitable container mean. Such separate packaging of the components in a suitable container mean is also described as a kit.

Therefore, the present invention is also directed to a kit for the treatment of evolving broncho-pulmonary dysplasia, said kit comprising: a) a pulmonary surfactant at a dose of 100 to 200 mg/kg and a pharmaceutically acceptable carrier or diluent in a first unit dosage form; b) budesonide at a dose of 0.1 to 1.5 mg/kg and a pharmaceutically acceptable carrier or diluent in a second unit dosage form; and c) container means for containing said first and second dosage forms.

The combination of the present invention which could be administered to the preterm neonate after birth according to conditions which shall be established by the skilled person in the art, is suitable to treat any form of evolving bronchopulmonary dysplasia.

The frequency of administration will vary with the size and gestational age of the preterm neonate, as well as with the severity of the neonate condition and the route of administration. Those of skill in the relevant art will be readily able to determine it.

For instance, the medicament of the invention could be administered once or twice a day.

Advantageously, the combination of the present invention is administered from the $2^{nd}$ to the $28^{th}$ day of life, preferably from the $5^{th}$ to the $15^{th}$ day of life, more preferably from the $7^{th}$ to the $10^{th}$ day of life.

Within the above interval time, the treatment could be continued for a period of time deemed by a physician or other medical practitioner as appropriate to achieve the therapeutic effect.

The preterm neonate requiring the medicament of the invention may or may not exhibit respiratory distress syndrome (RDS). In one embodiment, the administration of the medicament of the invention is initiated in a neonate exhibiting RDS, following treatment of such syndrome with pulmonary surfactant or by another means (e.g., ventilation) or a combination thereof.

In certain embodiments, neonates to be treated with the medicament of the present invention require respiratory support but do not necessarily exhibit respiratory distress syndrome. These infants either have not been diagnosed with RDS or have not been treated with pulmonary surfactants for RDS.

All pre-term neonates could be eligible for the administration of the medicament of the present invention including extremely-low-birth weight (ELBW), very-low-birth weight (VLBW), and low-birth weight (LBW) neonates of 24 to 35 weeks gestational age. Preferably, the medicament is administered to VLBW neonates with severe RDS who will have a higher incidence of BPD.

In general terms, since management of evolving BPD is unlikely to be in the form of a single intervention but rather a combined approach, the physician shall evaluate whether preterm neonates also require concomitant respiratory support and/or other suitable drugs such as vitamin A and antibiotics.

In view of the dosages of the pulmonary surfactant and budesonide and the volume of the formulation to be administered, discussed above, and the typical weight of the preterm neonate receiving the administration, the solution or suspension formulation will typically contain budesonide in a concentration of 0.05 to 0.5 mg/ml, preferably 0.1 to 0.25 mg/ml, and the pulmonary surfactant in a concentration of 20 to 100 mg/ml, preferably 40 to 80 mg/ml.

Other features of the invention will become apparent in the course of the following descriptions of exemplary embodiments which are given for illustration of the invention and are not intended to be limiting thereof.

EXAMPLES

Example 1. In Vitro Evaluation of the Surface Activity of Poractant Alfa in the Presence of Budesonide by Capillary Surfactometer The surface activity of poractant alfa (in the presence of budesonide, 2 ml, 1.0 mg) was evaluated in comparison to poractant alfa alone by a capillary surfactometer commercially available from Calmia Medical, Inc., USA.

Two samples were prepared: one from a vial of poractant alfa (1.5 ml, 80 mg/ml) by diluting with saline to a concentration 1 mg/ml in phospholipids, and the other from a vial of poractant alfa (1.5 ml, 80 mg/ml) mixed with a vial of budesonide (2 ml, 1.0 mg) and diluted with saline to the same concentration (1 mg/ml phospholipids). A 0.5 ml sample of both solutions was then assessed in the Capillary Surfactometer.

The principle of the capillary surfactometer was to simulate terminal human airways. The sample was introduced into the narrow section of a glass capillary, where the inner diameter is 0.25 mm, similar to that of a terminal human airway. At one end the capillary was connected to a bellows and a pressure transducer. When the bellows was slowly compressed, pressure is raised and recorded. The increasing pressure caused the sample to be extruded from the narrow section of the capillary. As air gets through, pressure was abruptly lowered. If the sample contained well-functioning pulmonary surfactant the sample liquid did not return to the narrow section. The steady airflow obtained by the continuous compression of the bellows met no resistance and the pressure recorded was zero. If on the other hand the sample did not contain a well-functioning pulmonary surfactant, the sample liquid returned repeatedly.

The behavior of poractant alfa in the presence of budesonide turned out to be statistically indistinguishable from that of poractant alfa alone, indicating that budesonide at said dose does not affect the surface activity of the surfactant.

Example 2. In Vivo Evaluation of the Activity of Poractant Alfa in the Presence of Budesonide in a Lamb Model of BPD An experiment for the study of neonatal resuscitation and lung injury with an assessment of a surfactant with budesonide treatment to decrease lung injury was performed. The experiment was aimed at checking whether a stretch injury to the fetal lung would modulate a second ventilation mediated injury 24 hours after intrauterine recovery.

This was a study to test for preconditioning or tolerance response potentials of the fetal lung. The treatment with surfactant with or without budesonide after the initial stretch injury was to test if the steroid had anti-inflammatory effects that would protect the fetal lung. The groups of animals included CPAP exposure and no initial exposure for comparison with the stretch injury. The groups and their characteristics and treatments are given in Table 1. The legend to Table 1 gives details about the interventions. FIG. 1 is a schematic of the protocol for this complex series of interventions.

TABLE 1

| Groups | Animal Number | Gestational Age | Fetal Lung injury Intervention | Treatment after Intervention | Ventilation Test at 24 hrs. | Birth Weight (kg) |
|---|---|---|---|---|---|---|
| CPAP + Surf + Vent | 5 | 125.8 | CPAP only | Surf + Saline | Yes | 2.9 |
| CPAP + Surf + Bud 0.25 mg · kg + Vent | 6 | 125.8 | CPAP only | Surf + Bud – 0.25 | Yes | 2.6 |
| $V_t$15 + Surf + Vent | 7 | 126 | Yes | Surf + Saline | Yes | 3.1 |
| $V_t$15 + Surf + Bud 0.25 mg/kg + Vent | 8 | 126.1 | Yes | Surf + Bud – 0.25 | Yes | 3.0 |
| $V_t$15 + Surf + Bud 1.0 mg/kg + Vent | 7 | 126.6 | Yes | Surf + Bud – 1 mg | Yes | 2.7 |
| Nothing + Vent | 6 | 126.3 | No | Nothing | Yes | 2.9 |
| Nothing + Nothing | 5 | 125.4 | No | Nothing | No | 2.8 |

Legend to Table

CPAP: Animals placed on 5 cm $H_2O$ CPAP for 15 min as a control for the anesthesia and surgery related to the injury intervention.

Fetal lung injury intervention: Yes=Head and chest of animal is exposed; 4.5 mm endotracheal tube is secured in the trachea. The fetus then is ventilated with 100% humidified nitrogen with R=30, IT=1 sec, PEEP=0, maximal pressure to 55 cm $H_2O$. The goal was to achieve an estimated $V_t$ of 7 ml/kg at 4 min, 12 ml/kg at 8 min, and 15 ml/kg at 12 min. The total period of ventilation was 15 min.

Pulmonary surfactant (Surf): After the CPAP or fetal lung injury intervention, animals were treated with 100 mg/kg Curosurf assuming 3 Kg weight. Curosurf plus budesonide was diluted with saline to 10 ml. Surfactant was given through endotracheal tube and mixed by syringe with fetal lung fluid. Following surfactant treatment, the trachea was ligated to prevent loss of surfactant.

Budesonide (Bud): Pulmicort Respules (Astra Zeneca, Sweden) containing 0.5 mg micronized budesonide in 1 ml was mixed with Curosurf plus saline to deliver 0.25 or 1.0 mg/kg budesonide and surfactant in a 10 ml suspension.

Ventilation test at 24 hours: Head of animal was again exposed and a 4.5 mm endotracheal tube was placed. Fetal lung fluid was aspirated by syringe and the lamb was delivered and ventilated with a rate of 40, an inspiratory time of 0.45 sec, a PEEP of 5 cmH$_2$O and a maximal peak inspiratory pressure of 40 cm H$_2$O with 100% humidified oxygen.

The experiment was designed for 46 fetal sheep, and the final total was 44 as one ewe had no fetus and one twin was a singleton. The experimental procedures were successfully completed with all other lambs. The number of animals per group were adjusted to increase the animals in the $V_t$ 15 injury and surfactant groups in order to increase statistical power for those groups. Specific comments about important elements of the experimental design follow.

The ventilation injury targeted to an estimated 15 ml/kg tidal volume at 15 min only achieved a volume of 11-13 ml/kg despite use of the maximal pressure of 55 cm H$_2$O, indicating that the fetal lungs were immature and surfactant deficient.

The $V_t$ injury and CPAP groups (assuming 3 kg birth weight) were administered with 100 mg/kg Curosurf or Curosurf plus budesonide diluted to 10 ml with saline. The trachea was ligated following treatment to assure that the treatments stayed in the lung for 24 hrs in utero prior to assessment of lung function.

Budesonide was used as 0.5 mg/ml Pulmicort Respules so as to have a standardized sterile product for exposure of the fetal lung.

At delivery 24 hrs after the initial intervention and treatment, an endotracheal tube was placed and any freely flowing fetal lung fluid was withdrawn with a syringe. Large amounts of fluid were recovered from CPAP exposed lungs. There was no fetal lung fluid and only small amounts of thick secretions were aspirated from the $V_t$ injured lungs.

The post-delivery ventilation period of 30 min was successful in all ventilated lambs. Some lungs had air collections within lung tissue and pleural blebs, but most of the pressure volume curves were successful.

Results

There were no important differences in gestational ages or birth weights between groups (Table 1). These experiments are complex to analyse because there are 7 groups. The Nothing+Nothing animals will be used only for tissue collection for the baseline measurements.

Oxygenation

Figure 2:
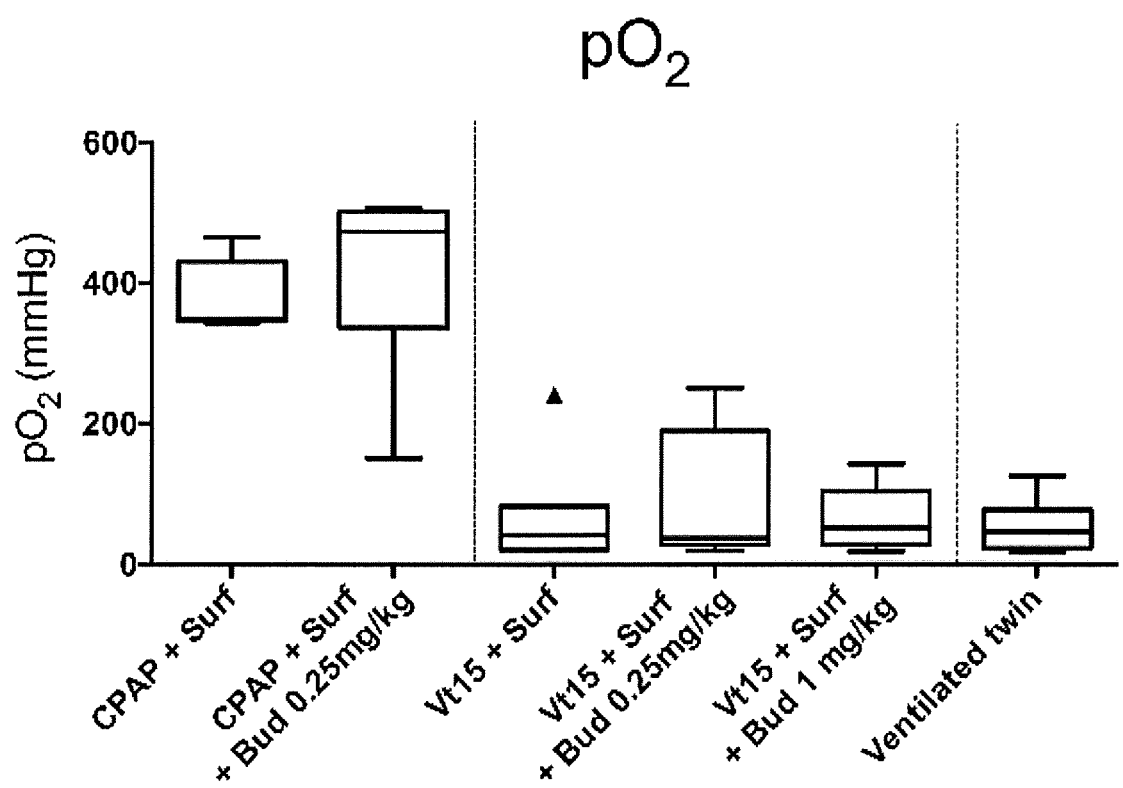
FIG. 2 shows the oxygenation results of Example 2.

The results are reported in FIG. 2.

Oxygenation measured as arterial PO$_2$ while the animals were ventilated with 100% oxygen, was very low for the uninjured and not surfactant treated ventilated twins only exposed to anaesthesia 24 hours before the ventilation— mean value 54 mmHg. This result verifies that the lambs had immature lungs prior to any intervention. Despite surfactant with or without budesonide, the injury ablated an oxygenation response. The 15 min CPAP+surfactant treatment resulted in a striking increase in mean PO$_2$ to 380 mmHg and the addition of budesonide resulted in a mean PO$_2$ of 417 mmHg, indicating that said addition slightly increases oxygenation.

In the non-ventilated groups, even though rather low, a slight improvement trend in presence of increasing concentration of budesonide can be appreciated from the comparison of groups median values.

Static Lung gas volume at 40 cmH$_2$O measured from the Pressure-Volume curves.

Figure 3:
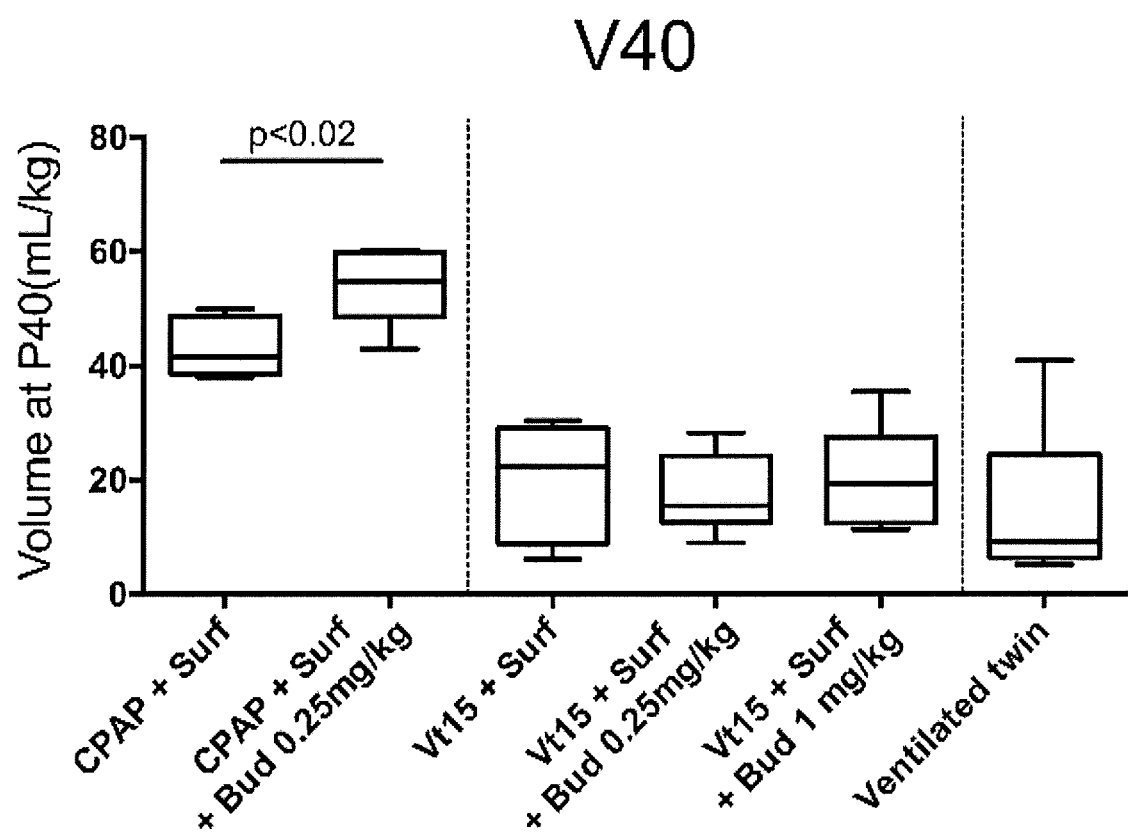
FIG. 3 shows the static lung gas volume at 40 $cmH_2O$ measured from the pressure-volume curves for Example 2.

The results are reported in FIG. 3.

The maximal lung gas volumes expressed relative to body weight measured following oxygen adsorption for inflation measurements on a lung without gas lung were low in the ventilated twin lungs. The CPAP+surfactant group had a large increase in lung gas volume/kg body weight, and budesonide significantly increased the volume relative to CPAP+surfactant. As for oxygenation, there were no large effects on lung gas volumes for animals in the $V_t$ 15 injured groups.

Lung Weight

Figure 4:
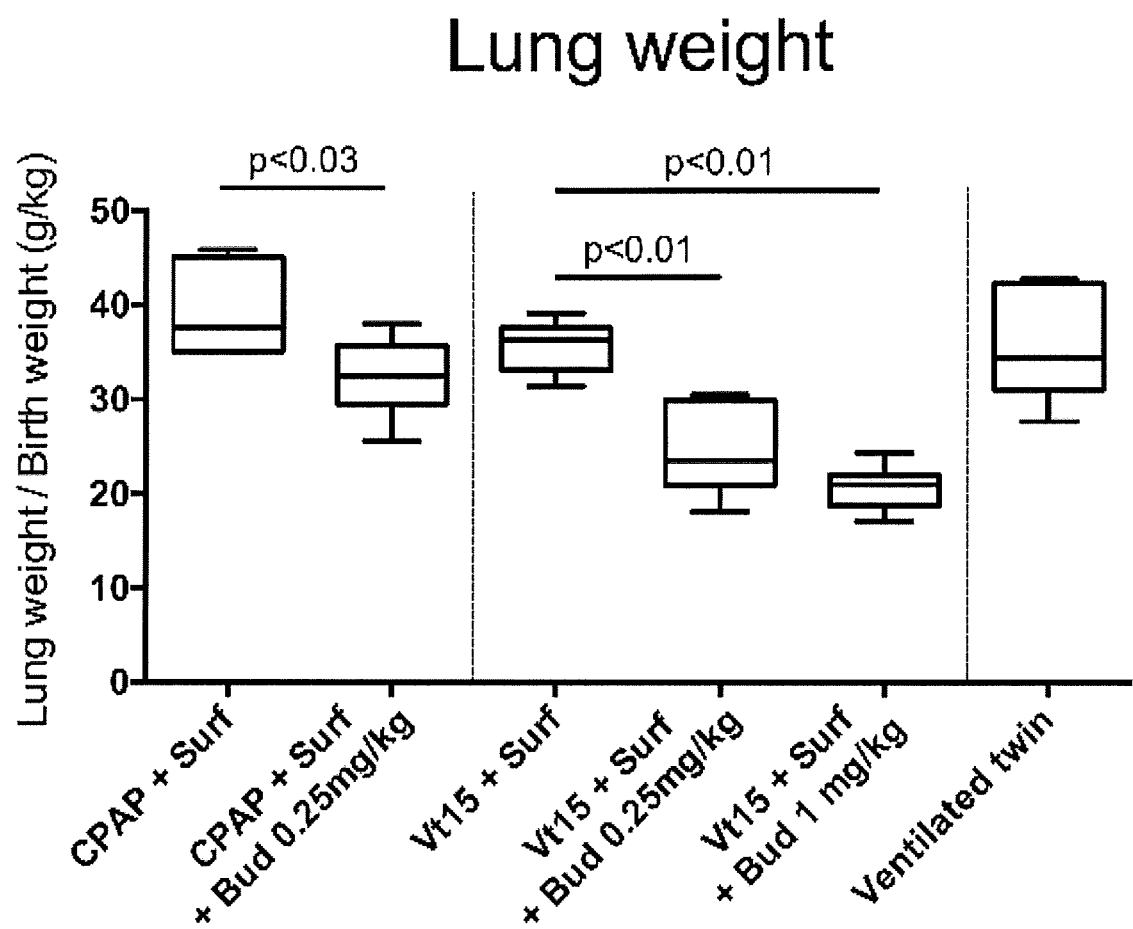
FIG. 4 shows the lung weight results for Example 2.

The results are reported in FIG. 4.

Large changes in lung weight across the groups at necropsy were surprisingly observed. Lung weights for the ventilated twin, the Vt 15 injury+surfactant and CPAP+surfactant were similar. However, in each of the budesonide groups, lung weights were lower with the largest effect noted for the 1.0 mg/kg budesonide group. Much change in lung weight with fetal exposure to maternal steroids was never measured in other experiments, so the observed very large changes in lung weights are rather unexpected.

Lung Gas Volume Relative to Lung Weight

Figure 5:
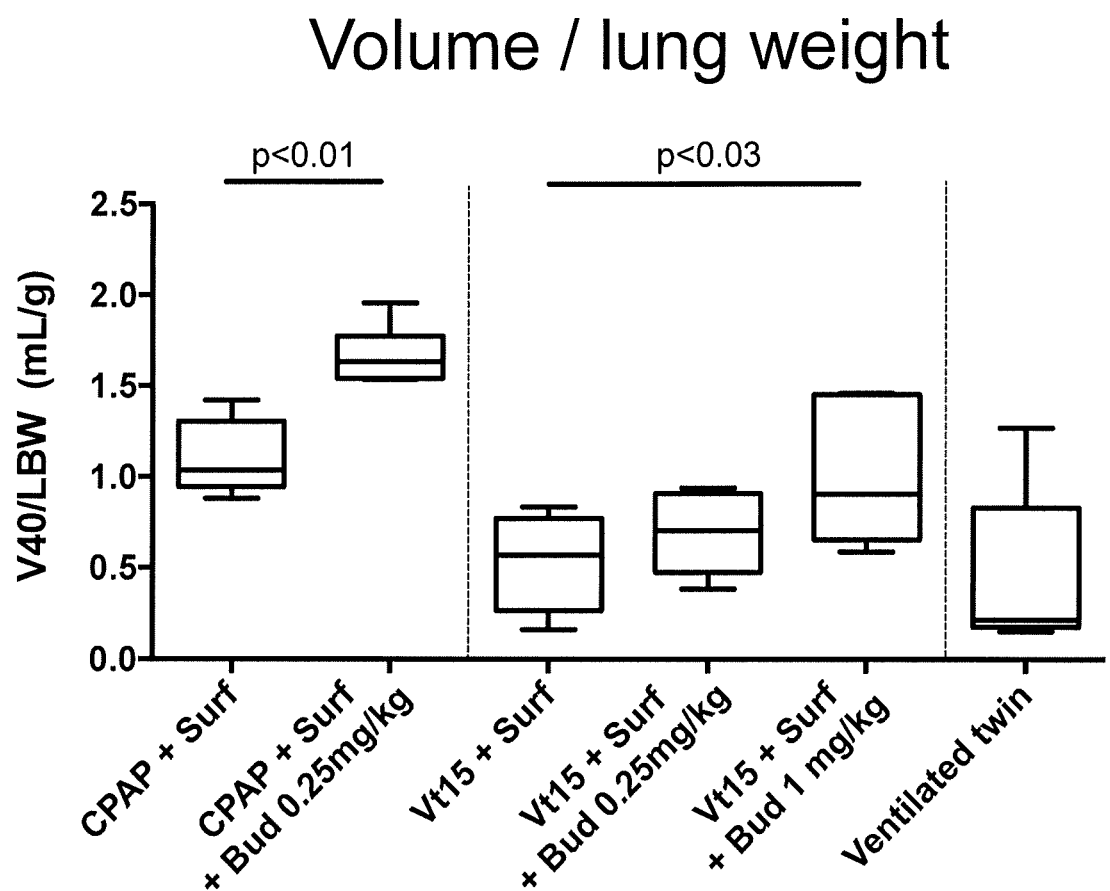
FIG. 5 shows the lung gas volume relative to lung weight for Example 2.

The results are reported in FIG. 5.

Of note, while lung weight decreased for the CPAP+surfactant+budesonide group relative to the CPAP+surfactant group, the lung gas volume increased. Therefore, the lung volume to lung weight ratios is shown. This ratio emphasizes the combined effects of lighter lungs that hold more gas. CPAP+Budesonide lungs held more gas than the CPAP lungs. This ratio also demonstrates that the $V_t$ 15+surfactant lung held less gas than those exposed to lung budesonide.

Lung Dry to Wet Weight Ratios

Figure 6:
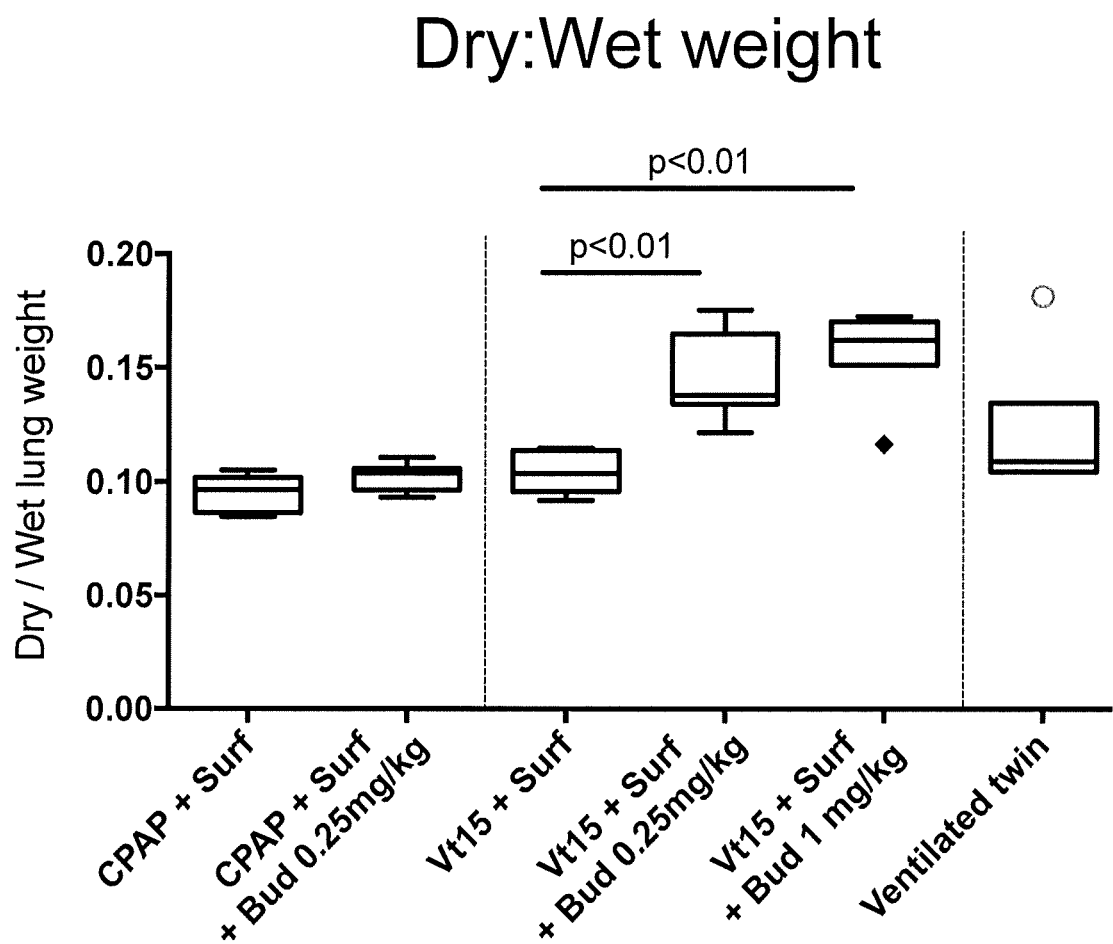
FIG. 6 shows the lung dry to wet weight ratios for Example 2.

The results are reported in FIG. 6.

These large changes in lung weight associated with budesonide must be primarily loss of lung water over 24 hours. That loss of water could indicate loss of mesenchymal cells and a maturation response.

mRNA Indicators of Lung Maturation mRNA was analyzed for surfactant proteins (SP) A, B, C, and D.

It is well known that the expression of the surfactant proteins are a sign of lung maturation.

Figure 7:
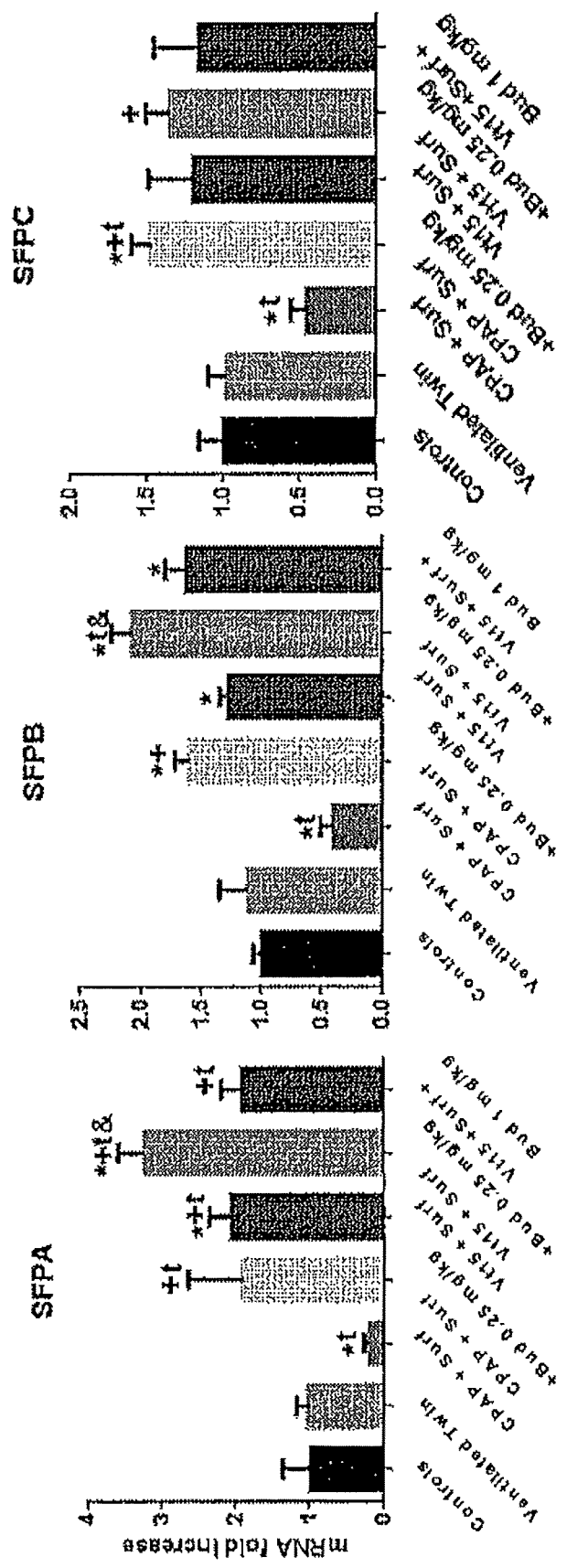
FIG. 7 shows the mRNA indicators of lung maturation SP-A, SP-B and SP-C results for Example 2.

The results for SP-A, SP-B, and SP-C, are reported in FIG. 7.

There were consistent decreases in mRNA for the CPAP+surfactant group relative to the unmanipulated controls and ventilated twins. Said suppression of surfactant protein mRNA is rather unexpected. Of interest, the combination of CPAP+surfactant with budesonide increased the surfactant proteins significantly.

Example 3. Formulation in Form of an Aqueous Suspension According to the Invention

| Ingredients | Quantity For pharmaceutical unit |
| --- | --- |
| Poractant alfa | 160 mg |
| micronised budesonide | 0.5 mg |
| Polysorbate (Tween) 20 | 2.0 mg |
| Sorbitan monolaurate | 0.4 mg |
| Sodium chloride | 18 mg |
| Water for injection q.s. for | 2.0 ml |

Example 4. Airway Thickness Determination

It is known that the large and small airway appearance and thickness is altered by both CPAP and mechanical ventilation.

In particular, in the lack of proper lung maturation, an increase of the wall thickness as well as an increase of collagen deposition is observed.

Therefore, the thickness of large airway/bronchioles and the collagen deposition was measured in lambs exposed to hyperoxia according to the method reported in Wang H et al Am J Physiol. Lung Cell Mol Physiol 2014, 307, L295-L301, which is incorporated herein by reference in its entirety.

The thickness was measured on blinded sections with 3 measurements per slide image, and 5 slide images per animal, and 4 to 6 animals per group.

The results are reported in Table 2.

Animals receiving mechanical ventilation had thickened small and large airways. Furthermore, quantification of collagen within the airways demonstrated increased collagen staining in animals receiving mechanical ventilation.

On the contrary, a decrease was observed for the CPAP+surfactant+budesonide groups, particularly significant for the CPAP+surfactant+budesonide 0.25 mg/kg group.

TABLE 2

| Groups | Large Airway Thickness Microns | Large Airway Collagen % staining | Bronchiole Thickness Microns | Bronchiole Collagen % staining |
| --- | --- | --- | --- | --- |
| CPAP + Surf + Vent | 65.4 ± 8.9* | 21.4 ± 5.7* | 16.3 ± 4.1 | 51.3 ± 13.5* |
| CPAP + Surf + Bud 0.25 mg · kg + Vent | 35.1 ± 7.1 | 7.4 ± 1.6 | 14.1 ± 1.9 | 22.9 ± 10.6 |
| $V_t15$ + Surf + Vent | 70.1 ± 7.9* | 29.4 ± 5.6* | 21.3 ± 5.5* | 84.8 ± 19.1* |
| $V_t15$ + Surf + Bud 0.25 mg/kg + Vent | 30.1 ± 7.6 | 8.3 ± 1.7 | 13.2 ± 2.7 | 14.6 ± 1.6 |
| $V_t15$ + Surf + Bud 1.0 mg/kg + Vent | 35.5 ± 4.1 | 18.2 ± 1.5* | 15.0 ± 0.4* | 40.0 ± 8.1* |
| Unventilated Controls | 28.7 ± 11.4 | 3.6 ± 1.1 | 11.3 ± 1.2 | 13.0 ± 3.3 |

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for the treatment of evolving bronchopulmonary dysplasia (BPD) in a preterm neonate, comprising administering to a preterm neonate at least one pulmonary surfactant in a dose of 100 to 200 mg/kg and budesonide in a dose of 0.1 to 0.5 mg/kg.

2. A method according to claim 1, wherein said pulmonary surfactant and budesonide are administered from the $2^{nd}$ to the $28^{th}$ day of life of the preterm neonate.

3. A method according to claim 1, wherein said pulmonary surfactant and budesonide are administered from the $5^{th}$ to the $15^{th}$ day of life.

4. A method according to claim 1, wherein said pulmonary surfactant and budesonide are administered from the $7^{th}$ to the $10^{th}$ day of life.

5. A method according to claim 1, wherein said preterm neonate is kept under a non-invasive ventilation procedure.

6. A method according to claim 1, wherein said non-invasive ventilation procedure is nasal CPAP.

7. A method according to claim 1, wherein said budesonide is administered at a dose of 0.2 to 0.5 mg/kg.

8. A method according to claim 1, wherein said at least one pulmonary surfactant and budesonide are administered simultaneously.

9. A method according to claim 1, wherein said at least one pulmonary surfactant and budesonide are administered sequentially.

10. A method according to claim 1, wherein said at least one pulmonary surfactant and budesonide are administered separately.

11. A method according to claim 1, wherein said at least one pulmonary surfactant comprises poractant alfa.

12. A method according to claim 1, wherein said administering is administration by inhalation or intratracheal route.

13. A method according to claim 1, wherein said at least one pulmonary surfactant and budesonide are administered in the form of an aqueous suspension comprising a pharmaceutically acceptable carrier.

14. A method according to claim 1, wherein said administering results in an increase in the mRNA expression of the proteins SP-A, SP-B, and SP-C.

* * * * *